United States Patent [19]

McNally

[11] Patent Number: 4,861,557
[45] Date of Patent: Aug. 29, 1989

[54] COMBUSTIBLE GAS DETECTOR THROUGH USE OF REACTION CONTROL BLOCK

[75] Inventor: Frank X. McNally, Venetia, Pa.

[73] Assignee: Industrial Scientific Devices, Inc., Oakdale, Pa.

[21] Appl. No.: 803,971

[22] Filed: Jan. 21, 1986

[51] Int. Cl.$^4$ ............................................. G01N 27/16
[52] U.S. Cl. ..................................... 422/97; 436/152
[58] Field of Search .................................. 422/94–97; 436/152, 159; 73/23, 27

[56] References Cited

U.S. PATENT DOCUMENTS

| | | | |
|---|---|---|---|
| 2,204,966 | 6/1940 | Morgan | 422/97 |
| 3,251,654 | 5/1966 | Palmer | 422/97 |
| 3,586,486 | 1/1971 | Kim et al. | 422/97 |
| 3,687,631 | 8/1972 | Zegel | 436/152 |
| 3,950,980 | 4/1976 | Braun et al. | 73/23 |

FOREIGN PATENT DOCUMENTS

| | | | |
|---|---|---|---|
| 92132 | 10/1983 | European Pat. Off. | 422/97 |
| 2088559 | 6/1982 | United Kingdom | 422/96 |

*Primary Examiner*—Michael S. Marcus
*Attorney, Agent, or Firm*—William J. Ruano

[57] ABSTRACT

Apparatus for detecting a combustible gas which comprises a Wheatstone bridge circuit having a detector element comprising an electrically conducting member coated with a refractory and having on the surface of said refractory a catalyst for the oxidation of said gas, said detector element constituting one leg of said bridge, and a reference element comprising an electrically conducting member coated with a refractory, said reference element constituting a second leg of said bridge, whereby upon catalytic oxidation of said gas an electrical signal approximately proportional to the amount of said gas present at the detector element is produced. The improvement comprises a reaction control block having a cover in the form of a dust shield and having two chambers, one containing said detector element, and the other containing said reference element. A partition is contained in said block parallel to and spaced from said dust shield to form a plenum space therebetween said partition having a pair of opening means, each communicating with one of said chambers to provide communication with said plenum space to limit the diffusion of the combustible gas so as to control the reaction rate at the detector element and improve the characteristic of the detector.

6 Claims, 1 Drawing Sheet

COMBUSTIBLE GAS DETECTOR THROUGH USE OF REACTION CONTROL BLOCK

This invention relates to an improved combustible gas detector through use of a reaction control block.

BACKGROUND OF THE INVENTION

Combustible gas detection instruments in use in industry today commonly employ a Wheatstone bridge configuration in the conventional manner by modifying two elements of the bridge. For example, one element would be a conventional refractory catalytic detector containing platinum whereby the combustible gas is burned, heating and increasing the resistance of the catalytic element, and the other element would be a refractory containing a poisoning element so that the combustible gas would not react. In this manner, a signal would be developed in the conventional manner as shown in FIG. 1.

A shortcoming of this type of construction is that the detecting elements contain a finite amount of catalytic material which can be inhibited with excessive exposure to combustible gases, such as methane. In the case of portable instruments, while it is not expected that they will be exposed to high levels of combustible gas (considering that they are usually portable and hand-held), nevertheless, at times, it is expected that the detector will be exposed to these high levels; therefore, the design of the detector should be adequate to withstand these high levels, maintaining stability at concentrations, for example, of 75% to 100% LEL (3.75 to 5% Vol. methane).

What happens during these high levels of combustible gas is that the burning gas reacts with air (oxygen) and the products of combustion are generally water and $CO_2$. During the high levels of gas combustion, the molecules are breaking down and uniting with air to ultimately form water and carbon dioxide, but intermediate compounds are the formation of hydroxides on the surface, these hydroxides temporarily uniting with the meta-stable alumina refractory and/or catalytic compounds. For example, in the following equation, during the burning of the combustible gas right at the surface of the catalyst, the very active state of the compounds may form temporary hydroxides (hydroxylation) on the active sites which inhibit the catalytic activity;

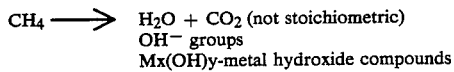

$CH_4 \longrightarrow H_2O + CO_2$ (not stoichiometric)
$OH^-$ groups
$Mx(OH)y$-metal hydroxide compounds The metal hydroxide compounds, or the hydroxide group forming at the refractory-carrier-catalyst active site, may blind or otherwise inhibit the activity of the site. At high methane concentrations, (2.5% to 5% Vol.), the reaction rate favoring the formation of such compounds at the active sites can increase. Upon removal of the high methane concentrations and exposure to clean air, the hydroxide groups leave and re-expose the active catalytic sites (dehydroxylation).

This can also be proven by exposing the detector to high concentrations of methane, for example, 90% Vol., when little or no burning occurs and the equilibrium then shifts to reducing and removal of the hydroxylated sites with formation of water, thus re-exposing the active catalytic site.

A similar action occurs, according to British Pat. No. 1,604,081, wherein advantage is tken of this dehydroxylation phenomenon by raising the temperature of the refractory, removing the hydroxide groups, generating active refractory catalytic sites, cooling, followed by immediate application of the catalyst within minues so that the catalyst gets to the active site before water molecules from the air, producing more and more stable catalytic sites rather than a site being jointly competed for by a water molecule and a catalyst atom.

It is evident that a large area meta-stable alumina refractory alone is not a sufficient catalyst for this application, nor are any noble metals (Pt, Rb, etc.) in the massive solid state. Rather, the catalytic noble metal must be dispersed (electronic bonds strained) on the large area refractory, forming a carrier-catalyst active site to produce suitably active catalysts.

One method of reducing the diffusion of the gas and what is employed sometimes in industry, is to make the dust shield finer, but this leads to easy plugging.

Another method of reducing the diffusion rate of the gas to the catalyst and sometimes employed industrially, is to coat the catalyst bead with further coats of non-reactive refractory. However, this method poses several thermal conductivity and thermal radiation problems tending to reduce the temperature of the catalytic bead non-uniformly with given power, toincrease power requiements, and, also, to introduce non-linearity problems as the temperature of the bead changes.

SUMMARY OF THE INVENTION

The present invention relates to a method of using a machined reaction control block to reduce the diffusion rate of methane so that the limiting reaction rate is determined by the control block and not by the available catalytic activity depending upon quantity or quantum efficiency of the catalyst on the refractory.

A high level of combustible gas may cause an unnecessarily high reaction rate—this, in turn, causing hydroxylation of the catalyst-carrier system. By controlling the diffusion of the combustible gas to the catalyst-carrier system by use of an orifice in the combustion block, in accordance with the present invention, the rate of reaction can be reduced while, at the same time, maintaining sufficient reaction rate for a suitable signal level.

DETAILED DESCRIPTION OF THE PREFERRED EMBODIMENT

Figure 1:
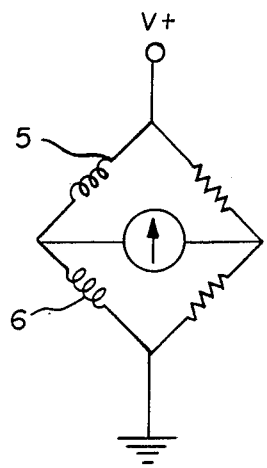
FIG. 1 shows a Wheatstone bridge in which the reaction control block of the present invention is used.
Figure 2:
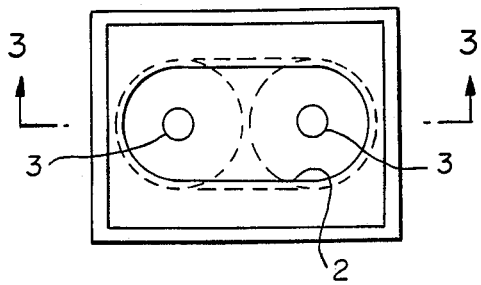
FIG. 2 is a top view of the reaction control block with the dust shield removed embodying the present invention.
Figure 3:
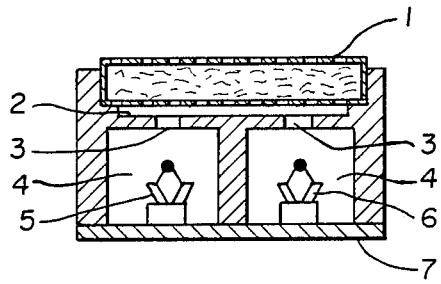
FIG. 3 is a vertical cross sectional view thereof taken along line 3—3 of FIG. 2.

In accordance with the present invention, and referring to FIGS. 2 and 3, after the gas diffuses through the dust shield 1, it enters a plenum space 2, enabling the entire area of the dust shield to permit diffusion of the gas which then enters the small orifices 3 into the combustion chamber 4 housing catalytic element 5 and reference element 6 supported by backplate 7. The diffusion is controlled and is reduced, and thus the rate of reaction and species of compounds forming at the catalyst-carrier active site is controlled.

An added feature of this design is that the orifice can be changed readily by starting with small holes and continuously enlarging them until the desired diffusion rate is obtained and, thus, the desired control of the reaction rate, which in turn controls the temperature, degree of hydroxylation, and magnitude of signal.

It can be readily visualized that without this orifice, and with the full impact of the gas on the elements, the burning of the gas would increase, the temperature would rise, and the signal would be larger, but a dynamic equilibrium would be shifted into favor of the formation of hydroxides or hydroxylation of the catalyst-carrier system. Further, the excessive rise in temperature with increasing gas concentrations results in higher burning efficiency producing positive non-linearity. Reducing the diffusion of the gas through the orifice reduces the quantity of the combustible gas, the reaction rate, and the formation of deleterious compounds. Whereas, the signal would be reduced, it is still adequate for processing in a suitable Wheatsone bridge amplification system.

An approximate method representing an active catalytic system would be:

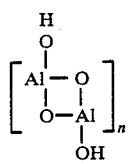

The absence of an OH radical would produce an active Lewis acid site, the number n being relatively small, whereas, if n were sufficiently large, there would be fewer opportunities for formation of active catalytic sites; i.e., sufficiently large n would progress toward $Al_2O_3$, low surface area alumina, which is considered a very poor catalyst carrier for the particular reactions required. Noble metals, and other catalytic metals which form hydroxides, would also exhibit the same phenomena.

If there is an excess of active sites to handle any flow of combustible gas, a percent decrease in catalytic activity may not be noticed and the term "catalyst limited" used. However, there may be less excess of sites and, thus, a percent degradation in catalytic activity is noticed. If now one attenuates the methane flow so that there is less methane, equal attenuation for all concentrations, the detectors will then maintain enough active sites for all concentrations, and the term "gas diffusion limited" is used.

The reaction control block enables the "gas diffusion limited" phenomenon to be readily exploited.

Figure 4:
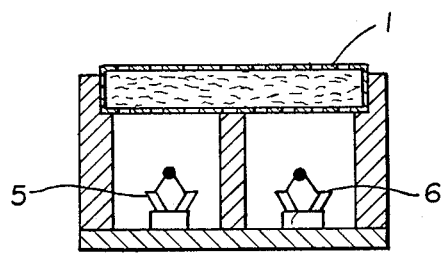
FIG. 4 shows a commonly used combustion chamber with direct exposure of the detecting elements to the combustible gas.

FIG. 4 illustrates the prior art design combustion chamber showing how the methane gas with low impedance passes through the dust shield 1 reaching the detecting catalytic element, where it burns, heating the element to high temperatures in a catalyst controlled mode, changing resistance of the coil, thus generating a signal. By employing a suitable restrictive and readily adjustable orifice size, a regulated amount of methane meets the element and in the diffusion limited mode.

Table 1, below, shows calculations comparing the diffusion of combustible gas (methane) in a conventional prior art combustible block with no orifice, to the prresent disclosure delineating the quantitative gas attenuation with various orifices.

TABLE 1
METHANE DETECTOR REACTION CONTROL BLOCK
Examples of Calculations $$\text{Diffusion Rate} = \frac{(X \text{ moles})}{(\text{sec})} \text{ methane}$$

The Present Invention
With Restricting Orifice (FIG. 3)
Effect of Varying Orifice Size

| | Diam. | Area | Total Diffusion Rate Mols/sec Methane |
|---|---|---|---|
| Prior Art No Orifice | 3/8" | .713 cm² | Assume 100(× mols)/sec (100%) |
| With Restricting Orifice | 1/16" | .0198" | 2.8(× mols)/sec (2.8%) |
| | 5/64" | .0308" | 4.3(× mols)/sec (4.3%) |
| | 3/32" | .0437" | 6.1(× mols)/sec (6.1%) |

Table 2, below, illustrates the difference between the prior art block (no orifice) and a reaction control block at different voltages. Notice that in air the different voltages provide the same operating temperature of the elements for the two blocks, but when 4 percent methane is introduced, the temperature is reduced considerably in the case of the catalyst element utilizing the reaction control block.

TABLE 2
DETECTOR OPERATING AND SIGNAL TEMPERATURE

| | | | | Coil Temperature | | | | |
|---|---|---|---|---|---|---|---|---|
| | | | | Catalyst | | | Reference | |
| Detector Block | Vbge | I | Watts | Air | 4% CH₄ | ΔT | Air | 4% CH₄ |
| Prior | 2.00 | .114 | .23 | 480 | 615 | 135 | 545 | 505 |
| Art | 2.10 | .118 | .24 | 505 | 640 | 135 | 575 | 530 |
| Block | 2.20 | .120 | .26 | 535 | 675 | 140 | 610 | 560 |
| This | 2.00 | .114 | .23 | 480 | 535 | 55 | 545 | 495 |
| Disclosure | 2.10 | .117 | .25 | 510 | 565 | 55 | 585 | 530 |
| Block | 2.20 | .120 | .26 | 535 | 590 | 55 | 610 | 550 |

$\Delta T$ = Catalyst Coil Temp. Using $\frac{4\% \text{ CH}_4}{615} - \frac{\text{Air}}{480} = 135°$ C.

One particular feature of prior art design is that current combustion chambers which do not inhibit the methane allow the temperature of the catalytic element to rise inordinately and non-proportonately when the percent methane concentration increases, and therefore, the detector is very non-linear. By the use of the reaction control block, the inordinate temperature rise is reduced and the detector is considerbly more linear.

Table 3, below, provides data on this effect; wherein the detectors were repeatedly tested for linearity with five concentrations of gas ten times. The result is very good and stable linearity.

TABLE 3
METHANE DETECTOR REACTION CONTROL BLOCK

Test: (a) Warm up detector 15 min.
(b) Expose to gas 45 sec.
(c) Expose to air 1 min.
(d) Repeat each gas -
Cycle: 1st up scale - then down scale 10 cycles

| Cycle | MV % CH$_4$ | MV % LEL | 1st Zero | % Methane Primary Standard Gases | | | | | last Zero | 5 gases |
|---|---|---|---|---|---|---|---|---|---|---|
| | | | | 1.00 | 2.01 | 2.56 | 2.96 | 4.02 | | |
| 1 | 9.7 | 0.48 | 0.0 | 1.0 | 2.0 | 2.6 | 3.1 | 4.2 | 0.0 | |
| 2 | | | 0.0 | 1.0 | 2.0 | 2.6 | 3.1 | 4.2 | 0.0 | |
| 3 | | | 0.0 | 1.0 | 2.0 | 2.6 | 3.1 | 4.1 | 0.0 | |
| 4 | | | 0.0 | 1.0 | 2.0 | 2.6 | 3.0 | 4.1 | 0.0 | |
| 5 | | | 0.0 | 1.0 | 2.0 | 2.6 | 3.0 | 4.1 | 0.1 | |
| 6 | | | 0.0 | 1.0 | 1.9 | 2.6 | 2.9 | 4.0 | 0.1 | |
| 7 | | | 0.1 | 1.0 | 1.9 | 2.5 | 2.9 | 4.0 | 0.1 | |
| 8 | | | 0.1 | 1.0 | 1.9 | 2.5 | 2.9 | 3.9 | 0.1 | |
| 9 | | | 0.1 | 1.0 | 1.9 | 2.5 | 2.9 | 3.9 | 0.1 | |
| 10 | 9.3 | 0.46 | 0.1 | 1.0 | 1.9 | 2.5 | 2.9 | 3.9 | 0.1 | |

While a single operning for each detector has been described, in some instances a plurality of such openings for each detector may be used instead, and while the openings have been illustrated as circular, they may be of other shapes instead. The openings may also be made variable by sliding a covering plate particularly thereover.

Thus it will be seen that I have provided an efficient and reliable apparatus for detecting a combustible gas with higher accuracy than heretofore obtainable.

While I have illustrated and described a single specific embodiment of my invention, it will be understood that this is by way of illustration only and that various changes and modifications may be contemplated in my invention within the scope of the followoing claims.

I claim:

1. In an apparatus for detecting a combustible gas which comprises a Wheatstone bridge circuit having a detector element comprising an electrically conducting member coated with a refractory having a surface, and having on said surface of said refractory a catalyst for the oxidation of said gas, said detector element constituting one leg of said bridge, and a reference element comprising an electrically conducting member coated with a refractory, said reference element constituting a second leg of said bridge, whereby upon catalytic oxidation of said gas an electrical signal approximately proportional to the amount of said gas present at the detector element is produced; the improvement which comprises a reaction control block having a cover in the form of a dust shield and having two chambers, one containing said detector element, and the other containing said reference element, and a partition which is contained in said block parallel to and spaced throughout its entire length from said dust shield to form a single continuous plenum space therebetween, said partition having a pair of opening means, each communicating with one of said chambers and with said continuous plenum space to provide communication with said continuous plenum space to limit the diffusion of the combustible gas so as to control the reaction rate at the detector element and improve the characteristic of the detector, said partition forming a cover totally enclosing said two chambers except for said opening means, said pair of openings being in unobstructed communication with each other through said plenum space.

2. Apparatus as recited in claim 1 wherein said opening means is a single opening for each chamber.

3. Apparatus as recited in claim 2 wherein said single opening is circular.

4. Apparatus as recited in claim 3 wherein said single opening has a diameter of about 1/16 inch to about 3/32 inch.

5. Apparatus as recited in claim 1 wherein said opening means has an area of between about 0.02 inch and about 0.045 inch.

6. Apparatus as recited in claim 1 wherein said opening means comprises a plurality of openings for each chamber.

* * * * *